United States Patent [19]

Arhancet

[11] Patent Number: 5,470,440

[45] Date of Patent: Nov. 28, 1995

[54] METHOD FOR INHIBITING VINYL AROMATIC MONOMER POLYMERIZATION

[75] Inventor: Graciela B. Arhancet, Katy, Tex.

[73] Assignee: Betz Laboratories, Inc., Trevose, Pa.

[21] Appl. No.: 230,032

[22] Filed: Apr. 19, 1994

[51] Int. Cl.$^6$ ..................................................... B01D 3/34
[52] U.S. Cl. ............................ 203/9; 203/56; 203/60; 203/65; 252/182.29; 252/183.12; 252/399; 585/5; 585/860; 585/864; 585/865; 585/950
[58] Field of Search ........................... 203/9, 8, 65, 60, 203/59, 58, 56; 585/950, 3, 4, 5, 860, 864, 865; 208/48 AA, 48 R; 252/399, 182.29, 183.12

[56] References Cited

U.S. PATENT DOCUMENTS

| | | | |
|---|---|---|---|
| 2,399,340 | 4/1946 | Franz | 203/9 |
| 4,062,545 | 12/1977 | Watson | 203/9 |
| 4,105,506 | 8/1978 | Watson | 203/9 |
| 4,177,110 | 12/1979 | Watson | 203/9 |
| 4,237,326 | 12/1980 | Fuga et al. | 203/9 |
| 4,466,905 | 8/1984 | Butler et al. | 252/403 |
| 4,774,374 | 9/1988 | Abruscato et al. | 585/24 |
| 4,915,873 | 4/1990 | Abruscato et al. | 252/402 |
| 4,929,778 | 5/1990 | Roling | 585/3 |
| 5,342,505 | 8/1994 | Forester | 208/48 AA |

*Primary Examiner*—Wilbur Bascomb, Jr.
*Attorney, Agent, or Firm*—Alexander D. Ricci; Philip H. Von Neida

[57] ABSTRACT

Vinyl aromatic monomer polymerization methods utilizing a composition of 2,6-di-tert-butyl-4-methylphenol and a substituted benzoquinonediimide compound are disclosed. Preferably, the composition is employed in an amount of 1 part to 10,000 parts per million parts monomer during distillation of styrene.

9 Claims, No Drawings

METHOD FOR INHIBITING VINYL AROMATIC MONOMER POLYMERIZATION

FIELD OF THE INVENTION

This invention relates to methods and compositions for inhibiting the unwanted polymerization of vinyl aromatic monomers.

BACKGROUND OF THE INVENTION

Common industrial methods for producing styrene typically include separation and purification processes such as distillation to remove unwanted impurities. Unfortunately, purification processes carried out at elevated temperatures result in an increased rate of undesired polymerization. Distillation is generally carried out under vacuum to minimize loss of monomer. The presence of oxygen, although virtually excluded in styrene distillation, will also promote polymerization of the monomer.

This polymerization results not only in loss of desired monomer end-product, but also in the loss of production efficiency caused by polymer formation and/or agglomeration of polymer on process equipment. Thermal polymerization of styrene monomer results in the formation of normal (i.e., linear) polymer. This resulting polystyrene polymer is characterized by its glassy and transparent appearance and its solubility in the styrene monomer and many organic solvents.

SUMMARY OF THE INVENTION

The present invention relates to methods for inhibiting the polymerization of vinyl aromatic monomers, such as styrene, and compositions comprising the synergistic combination of actives. The present inventor has discovered that a composition comprising 2,6-di-tert-butyl-4-methylphenol and a benzoquinone diimide compound will effectively inhibit the unwanted polymerization of vinyl aromatic monomers during their processing.

DESCRIPTION OF THE RELATED ART

U.S. Pat. No. 4,929,778, teaches methods and compositions for inhibiting the polymerization of styrene monomer during high temperature processing and storage thereof utilizing a phenylenediamine compound and a hindered phenol compound.

U.S. Pat. No. 4,774,379 teaches processes and compositions for inhibiting the polymerization of a vinyl aromatic compound utilizing an oxygenated species formed by the reaction of oxygen and an N-aryl-N' -alkyl-p-phenylenediamine. U.S. Pat. No. 4,915,873 teaches inhibiting vinyl aromatic monomer polymerization utilizing a phenothiazine compound and a phenylenediamine compound.

U.S. Pat. No. 4,061,545 teaches the combination of tert-butyl pyrocatechol and phenothiazine as a polymerization inhibitor in the presence of oxygen. U.S. Pat. No. 4,466,905 teaches the use of 2,6-dinitro-p-cresol and either a phenylenediamine compound or tert-butyl pyrocatechol to inhibit polymerization in the presence of oxygen.

A variety of inhibitor compositions have been employed in styrene and other vinyl aromatic monomers to inhibit undesirable polymerization. Amongst others, agents that have been used include sulfur, p-benzoquinone, phenylenediamines, tert-butyl pyrocatechol, phenothiazine, hydroxylamines, nitro compounds, and hindered phenols. However, many of these compounds present disadvantages such as high toxicity, instability and explosion hazard under elevated temperature, or insufficient efficacy under processing conditions (i.e., inhibitor requires oxygen to be effective). The present inventor has discovered a novel method and composition for inhibiting vinyl aromatic monomer polymerization that avoids these problems associated with known inhibitors.

DETAILED DESCRIPTION OF THE INVENTION

The present invention relates to methods for inhibiting the undesired polymerization of vinyl aromatic monomers utilizing a novel composition comprising 2,6-di-tert-butyl-4-methylphenol (BHT) and a substituted benzoquinonediimide compound.

The benzoquinonediimide compound has the general formula:

wherein $R_1$ and $R_2$ are the same or different and are alkyl, aryl, alkaryl, or aralkyl groups. Preferably, these groups have one to about 20 carbon atoms and the alkyl groups can be straight-chained, branch-chained, or cyclic groups.

Preferred benzoquinonediimide compounds include N,N'-dialkyl-benzoquinonediimides such as N,N'-di-sec-butyl-p-benzoquinonediimide; N-phenyl-N'-alkyl-benzoquinonediimides such as N-phenyl-N'-methyl-benzoquinonediimide, N-phenyl-N'-ethyl-benzoquinonediimide, N-phenyl-N'-propyl-benzoquinonediimide, N-phenyl-N'-n-butyl-benzoquinonedi-imide, N-phenyl-N'-isobutyl-benzoquinonediimide, N-phenyl-N'-sec-butyl-benzoquinonediimide, N-phenyl-N'-tert-butyl-benzoquinonediimide, N-phenyl-N'-n-pentyl-benzoquinonediimide, N-phenyl-N'-n-hexyl-benzoquinonediimide, N-phenyl-N'-(1-methylhexyl)-benzoquinonediimide, and N-phenyl-N'-(1,3-dimethylhexyl)-benzoquinonediimide.

The compositions of the present invention prove effective at inhibiting the polymerization of vinyl aromatic monomers undergoing processing, such as distillation and purification, conditions. The compositions surprisingly show efficacy in systems that are substantially oxygen free, which is typical of styrene distillation systems.

The total amount of 2,6-di-tert-butyl-4-methylphenol (BHT) and benzoquinonediimide compound used in the methods of the present invention is that amount which is sufficient to effect inhibition of polymerization and will vary according to the conditions under which the vinyl aromatic monomer is being processed and exposed to high temperatures. At higher processing temperatures, larger amounts of polymerization inhibiting treatment are generally required.

Preferably, the total amount of the combined treatment (BHT and benzoquinonediimide compound) is from about 1 part to about 10,000 parts combination treatment per million parts by weight of vinyl aromatic monomer. More preferably, the total amount of treatment employed as a polymerization inhibitor ranges from about 5 parts to about 500 parts per million parts by weight of vinyl aromatic monomer.

The composition of BHT and benzoquinonediimide compound is generally in a weight ratio range of 1:19 to 19:1. Preferably, the weight ratio of BHT and benzoquinonediimide compound is 1:1.

The BHT and benzoquinonediimide compound can be added to the vinyl aromatic monomer by any conventional method. The two components may be added individually or as a combination treatment. It is preferred to add the composition as a single treatment composition comprising both of the active vinyl monomer polymerization inhibitors.

Accordingly, it is possible therefore to produce a more effective vinyl aromatic monomer polymerization inhibition treatment than is obtainable by the use of either ingredient alone when measured at comparable treatment levels. This enhanced activity allows for the concentration of each of the ingredients to be lowered and the total quantity of polymerization inhibitor required at elevated temperatures may be reduced.

The inventive composition may be added to the vinyl aromatic monomer as either a dispersion or as a solution using a suitable liquid carrier or solvent. Any solvent that is compatible with both the vinyl aromatic monomer and the process may be employed, for example, a non-polar organic solvent.

The preferred inventive embodiment employs BHT in combination with N-(1,4-dimethylpentyl)-N'-phenyl-p-benzoquinonediimide, a mixture of N-(1,4-dimethylpentyl)-N'-phenyl-p-benzoquinonediimide and N-(1,3-dimethylbutyl)-N'-phenyl-p-benzoquininediimide, and N,N'-di-sec-butyl-p-benzoquinonediimide, respectively. These diimides can be obtained by oxidation of commercially available p-phenylenediamine compounds.

This invention will now be further described with reference to a number of specific examples which are to be regarded solely as illustrative, and not as restricting the scope of the invention.

EXPERIMENTAL

Benzoquinonediimide compounds used in the polymerization test without purification are identified as:

Diimide I: N-(1,4-dimethylpentyl)-N'-phenyl-p-benzoquinonediimide

Diimide II: mixture of N-(1,4-dimethylpentyl)-N'-phenyl-p-benzoquinonediimide and N-(1,3-dimethylbutyl)-N'-phenyl-p-benzoquinonediimide Diimide III: N,N'-di-sec-butyl-p-benzoquinonediimide Uninhibited styrene (100.0 ml) was placed in a 250-ml three-necked flask fitted with a bubbler, a septa, and, a condenser. The appropriate treatment was added and argon was bubbled through the solution at 10 ml/min for 10 minutes. Then, while argon sparging continued, the flask was immersed in an oil bath heated at 100° C. Samples (5.0 ml) were taken every 30 minutes and the amount of polymer formed was determined by methanol precipitation. The results of this testing are presented in Tables I and II.

TABLE I

Styrene polymerization under argon test
Treatment A is 25 ppm diimide 1:25 ppm BHT
Treatment B is 50 ppm diimide 1:50 ppm BHT

| Time (min) | % Polymer (weight) Treatment A | % Polymer (weight) Treatment B |
| --- | --- | --- |
| 30 | 0.05 | 0.00 |
| 60 | 0.08 | 0.00 |
| 90 | 0.21 | 0.01 |
| 120 | 0.32 | 0.04 |

TABLE II

Styrene polymerization under argon test
Treatment: 100 ppm, 1:1 diimide II: BHT

| Time (min) | % Polymer (weight) |
| --- | --- |
| 30 | 0.01 |
| 60 | 0.07 |
| 90 | 0.18 |
| 120 | 0.29 |
| 150 | 0.44 |

The results in Table I indicate that the combination of BHT and benzoquinonediimide compound provide effective polymerization inhibition in styrene monomer. At higher dosages (100 ppm), almost no polymer was formed.

Another benzoquinonediimide compound and BHT combination provided effective polymerization inhibition in styrene as seen in Table II. Further testing was performed comparing the polymerization inhibition ability of each individual component versus the enhanced inhibition activity of the BHT: benzoquinonediimide compound combination.

Uninhibited styrene (5.0 ml) with the appropriate treatment was placed in a test tube capped with a septum. Using two needles, argon was bubbled through the solution for at least 3 minutes. The tube was then placed in an oil bath heated to 100° C. for 2 hours. The amount of polymer formed was determined by methanol precipitation. The results of this testing are shown in Table III.

TABLE III

| Inhibitor (ppm) | % Polymer (weight) |
| --- | --- |
| None (0) | 4.86 |
| BHT (50) | 4.68 |
| Diimide I (50) | 3.89 |
| Diimide I/BHT (25:25) | 1.66 |
| Diimide III (50) | 4.11 |
| Diimide III/BHT (25:25) | 0.00 |

These results indicate the enhanced activity of the combination at polymerization inhibition over that of either component employed alone. Marked improvement can be seen when BHT is combined with either diimide compound.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what I claim is:

1. A method for inhibiting the polymerization of vinyl aromatic monomers during their distillation comprising adding to said monomers an effective polymerization inhibiting amount of a combination of 2,6-di-tert-butyl-4-methylphenol and at least one substituted benzoquinonediimide compound.

2. The method as claimed in claim 1 wherein said substituted benzoquinonediimide compound has the formula:

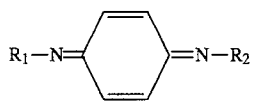

wherein $R_1$ and $R_2$ are the same or different and are alkyl, aryl, alkaryl, or aralkyl groups having one to about 20 carbon atoms.

3. The method as claimed in claim 1 wherein said substituted benzoquinonediimide compound is selected from the group consisting of N-(1,4-dimethylpentyl)-N'-phenyl-p-benzoquinonediimide and N,N'-di-sec-butyl-p-benzoquinonediimide.

4. The method as claimed in claim 1 wherein said at least one substituted benzoquinonediimide compound is a mixture of two or more substituted benzoquinonediimide compounds.

5. The method as claimed in claim 4 wherein said mixture comprises N-(1,4-dimethylpentyl)-N'-phenyl-p-benzoquinonediimide and N-(1,3-dimethylbutyl)-N'-phenyl-p-benzoquinonediimide.

6. The method as claimed in claim 1 wherein said combination is added to said monomer in a solvent.

7. The method as claimed in claim 6 wherein said solvent is a non-polar organic solvent.

8. The method as claimed in claim 1 wherein said combination is added to said amount in an amount ranging from 1 part to 10,000 parts per million parts monomer.

9. The method as claimed in claim 1 wherein said vinyl aromatic monomer is styrene.

* * * * *